US009700061B2

(12) United States Patent
Dalemans et al.

(10) Patent No.: US 9,700,061 B2
(45) Date of Patent: Jul. 11, 2017

(54) MILK INGREDIENT ENRICHED IN POLAR LIPIDS AND USES THEREOF

(75) Inventors: Daniel Dalemans, Herstal (BE);
Christophe Blecker, Forville (BE);
Pascal Bodson, Gembloux (BE);
Sabine Danthine, Couthuin (BE);
Claude Deroanne, Perwez (BE);
Michel Paquot, Noville sur Mehaigne (BE)

(73) Assignee: S.A. CORMAN, Goe (BE)

( * ) Notice: Subject to any disclaimer, the term of this patent is extended or adjusted under 35 U.S.C. 154(b) by 762 days.

(21) Appl. No.: 12/306,621

(22) PCT Filed: Jul. 13, 2007

(86) PCT No.: PCT/EP2007/057247
§ 371 (c)(1),
(2), (4) Date: Sep. 24, 2009

(87) PCT Pub. No.: WO2008/009636
PCT Pub. Date: Jan. 24, 2008

(65) Prior Publication Data
US 2010/0068293 A1      Mar. 18, 2010

(30) Foreign Application Priority Data

Jul. 17, 2006   (EP) ...................................... 06117336

(51) Int. Cl.
| A23C 9/142 | (2006.01) |
| A23C 9/13 | (2006.01) |
| A21D 2/32 | (2006.01) |
| A23C 13/12 | (2006.01) |
| A23C 19/082 | (2006.01) |

(52) U.S. Cl.
CPC .............. *A23C 9/1307* (2013.01); *A21D 2/32* (2013.01); *A23C 13/12* (2013.01); *A23C 19/082* (2013.01); *A23C 2240/05* (2013.01)

(58) Field of Classification Search
None
See application file for complete search history.

(56) References Cited

U.S. PATENT DOCUMENTS

| 5,223,299 A |   | 6/1993 | Dalan et al. |   |
|---|---|---|---|---|
| 5,844,104 A | * | 12/1998 | Yanahira et al. | ............ 536/18.5 |
| 2006/0280779 A1 |   | 12/2006 | Burling et al. |   |

FOREIGN PATENT DOCUMENTS

| GB | 1151879 |   | 5/1969 |
|---|---|---|---|
| JP | 3-47192 |   | 2/1991 |
| JP | 2001-275614 |   | 10/2001 |
| JP | 2005-27621 |   | 2/2005 |
| NZ | 314620 |   | 6/1998 |
| WO | WO 01/78518 | * | 10/2001 |
| WO | WO 01/78518 A2 |   | 10/2001 |
| WO | WO 02/34062 |   | 5/2002 |
| WO | WO 02/34062 A1 |   | 5/2002 |
| WO | WO 03/071875 |   | 9/2003 |
| WO | WO 03/071875 A1 |   | 9/2003 |
| WO | 2006/041316 |   | 4/2006 |
| WO | WO 2006/041316 |   | 4/2006 |

OTHER PUBLICATIONS

"Butter Manufacture" website (http://web.archive.org/web/20060621043002/http://www.foodsci.uoguelph.ca/dairyedu/butter.html—internet archived version from Jun. 21, 2006).*
English translation of Miura (JP 2005-027621—English translation)—2005.*
Sachdeva et al., "Recovery of phospholipids from buttermilk using membrane processing," *Kieler Wirtschaftliche Forschungsberichte*, Verlag Th. Mann, Gelsenkirchen, DE vol. 49, No. 1 (1997). 47-68. XP001014232.
Vesper et al., "Sphingolipids in food and the emerging importance of sphingolipids to nutrition," *J. Nutr.* (1999) 129: 1239-1250.
Rombaut et al., "Properties, analysis and purification of milk polar lipids", *International Dairy Journal*, vol. 16, 2006, pp. 1362-1373.
Sachdeva et al., "Recovery of phospholipids from buttermilk using membrane processing", *Kieler Milchwirtschaftliche Forschungsberichte*, vol. 49, No. 1, 1997, pp. 47-68.
Statements of Grounds and Particulars from Australian Application No. 2007276203 dated Jun. 13, 2013.
Affidavit of Christine Lennon Buchan dated Sep. 13, 2013.
Affidavit of Geoffrey Welsford Smithers dated Aug. 28, 2013.
Affidavit of David Scott Munro dated Oct. 8, 2013.
Affidavit of Philip Joseph Silvester dated Oct. 8, 2013.
Second Affidavit of Geoffrey Welsford Smithers dated Oct. 11, 2013.

* cited by examiner

*Primary Examiner* — Susan Hoffman
(74) *Attorney, Agent, or Firm* — Merchant & Gould P.C.

(57) ABSTRACT

A milk ingredient is enriched in polar lipids, in particular in phospholipids and in sphingolipids, in which the percentage of phospholipids is greater than 10% by weight, relative to the weight of solids of the ingredient, and a method obtains the same starting from pasteurized cream and is used in food and/or pharmaceutical products.

7 Claims, 7 Drawing Sheets

MILK INGREDIENT ENRICHED IN POLAR LIPIDS AND USES THEREOF

This application is a National Stage Application of PCT/EP2007/057247, filed Jul. 13, 2007, which claims benefit of Ser. No. 06117336.5, filed Jul. 17, 2006 in the EPO and which application(s) are incorporated herein by reference. To the extent appropriate, a claim of priority is made to each of the above disclosed applications.

OBJECT OF THE INVENTION

The present invention relates to a milk ingredient enriched with components of the membrane of fat milk globules, i.e. enriched in polar lipids, in particular in phospholipids and sphingolipids.

The present invention also relates to the method for obtaining such a milk ingredient enriched in components of the milk fat globules membrane from a pasteurized milk cream.

The last aspect of the present invention also relates to the advantageous application of said milk ingredients, as dietary supplements in food compositions, in pharmaceutical compositions or cosmetic compositions.

TECHNOLOGICAL BACKGROUND AND STATE OF THE ART AT THE BASIS OF THE INVENTION

It has been known for many years that food products have implications on the health of the consumer.

In particular, excessive consumption of fats in the human diet may cause the occurrence of serious pathologies notably generated by an increase in blood cholesterol and triglycerides, more specifically cholesterol.

In order to improve the health condition of the consumer, new low-fat products have been proposed, which unfortunately do not have the same organoleptic properties as the standard products.

The use of products defined as <<functional food>> has also been proposed which are made up from food products having a therapeutic or prophylactic effect within the scope of a supplement to the treatment and/or prevention of different pathologies (osteoporosis, cardiovascular diseases, cancer . . . ).

Such food ingredients for example consist of sugars, proteins, minerals or vitamins capable of improving or sustaining human health.

Document WO02/34062 describes a method for obtaining a product enriched in phospholipids and sphingolipids by ultrafiltration on a membrane having a cutoff value comprised between 5,000 and 20,000 Da and preferably depleted in or without any casein. In this document, with a concentration of sphingolipids (phospholipids, sphingomyelin) obtained by ultrafiltration of lactic buttermilk from butter factories, optionally deproteinized, or of a cheese industry/fresh cheese lactoserum, it is possible to obtain a milk ingredient enriched in polar lipids, in which the percentage of the phospholipids is less than 3% by weight relatively to the dry matter weight of the ingredient. This patent application also describes food products or food supplements comprising the product enriched in the obtained phospholipids and sphingolipids.

International patent application WO03/071875 describes a method for preparing from a cheese factory lactoserum, a concentrate enriched in milk polar lipids, in particular a concentrate enriched in milk sphingolipids from a cheese factory lactoserum. This device describes the use in parallel of ultrafiltration and diafiltration methods by means of 30,000 Da or 10,000 Da membranes. This method requires a preliminary proteolysis step (enzymatic hydrolysis of the proteins) of the raw material used (ultrafiltered cheese factory lactoserum). With this method, it is possible to obtain a concentrate enriched in sphingolipids (Ultra High Fat Concentrate—UHFC) which may then be treated with a phospholipase, in order to purify the obtained sphingolipids. However, the concentration of phospholipids in the obtained milk ingredient (by weight relatively to the dry matter weight of the ingredient), is less than 20%.

In addition, the obtained concentrated product will have deteriorated organoleptic properties due to the presence of peptide compounds originating from the proteolysis.

Furthermore, this document also describes a concentration method by ultrafiltration (in parallel), which is applied after enzymatic hydrolysis of the proteins. This enzymatic hydrolysis enables the protein fractions (peptides) to cross the ultrafiltration membrane and to be separated from the lipid fraction which remains retained by this membrane.

SACHDEVA et al. (in KIELER WIRTSCHAFTLICHE FORSCHUNGSBERICHTE VERLAG TH. MANN GELSENKIRCHEN, Volume 49 No. 1 1997 pp. 47-68) describe a method for recovering phospholipids from buttermilk by a chemical or physical treatment method. In this method, the raw material is sweetcream buttermilk powder which is submitted to a coagulation by adding rennet, citric acid or a lactic culture and calcium chloride, followed by a separation and a concentration of the serum through a membrane treatment by means of an ultrafiltration or a microfiltration. The obtained concentrate is a milk ingredient enriched in phospholipids in which the phospholipids percentage is less than 20% by weight relatively to the dry matter weight of the ingredient.

Japanese Application JP03/047192 describes a method of fractionation and purification of a phospholipids fraction derived from milk or from a dairy product, by using a centrifugal liquid-liquid partition (or sharing) chromatography step.

The extracts described in this patent application have purities greater than 80% or even 90%, but have been obtained by extractions with solvents (ether and acetone). The yields are unknown since the phospholipid concentration of the initial buttermilk is not given.

By applying centrifugal liquid-liquid partition chromatography in the presence of other solvents, the phospholipids may be separated and compounds purified at 97-98% are obtained, but the recovered amounts are less than one milligram (a laboratory technique).

Japanese Patent Application 2005 027 621 describes a method for purifying phospholipids from milk or from a dairy product by submitting these products to a microfiltration treatment by using membranes with a pore size comprised between 1 and 2 µm. With this method, it is possible to obtain a product having more than 30% by weight of phospholipids, optionally more than 35% by weight of phospholipids, this percentage being calculated on the basis of the dry matter of the composition (total dry extract). Furthermore, this document describes that, if the phospholipid concentration is greater than 35% by weight, it is possible to use the composition of the invention as an emulsifier.

This patent application describes a method for concentrating phospholipids by microfiltration of skimmed milk (defatted milk); a skimmed milk only contains the small fat globules alone, for which the <<surface/volume>> ratio is greater, which are therefore richer in phospholipids than the membrane lipids. The milk microfiltration method is traditionally used for removing the microorganisms. The obtained extract is washed and the phospholipid-enriched portion is recovered after breaking the emulsion. However, microfiltration of whole milk does not work, because it concentrates the fat in its integrality (no increase in the total phospholipid/fat ratio). Furthermore, by treating a very large amount of skimmed milk (which only contains 0.1% of fat) and from which only the agglomerates of fat globules, with a size larger than 2 µm, are recovered for obtaining small amounts of recovered phospholipids (20 metric tons of skimmed milk for recovering 200 g of a phospholipids-rich extract). Furthermore, the treatment also concentrates microbiological pollutants, which leads to mandatory washing, but this washing perhaps does not suppress all the risks.

The Japanese Patent Application JP2001 27 56 14 describes a composition containing phospholipids capable of having an advantageous action on the reduction of blood cholesterol and triglycerides, and an inhibiting action on the accumulation of neutral lipids in the liver. Additionally, a link between the disorders of the lipid metabolism and diabetes is also suggested in this document. Phospholipids used in this document are optionally obtained by known methods such as extraction by a solvent and the fractionation using different chromatographic means.

Aims of the Invention

The present invention is directed to obtain a milk ingredient enriched in lipidic components of the milk fat globule membrane, i.e. enriched in polar lipids, in particular in phospholipids and in sphingolipids and having particular physical properties but also and always including the characteristics of a milk ingredient, i.e. also substantially without any hydrolyzed proteins, while maintaining or improving typical organoleptic properties of a milk ingredient.

The present invention also aims to increase the organoleptic or structural properties of food compositions incorporating these ingredients and to provide an adequate daily dose of said polar lipids, in particular sphingolipids, so as to sustain or improve a satisfactory health condition of the consumer.

A particular aim of the present invention is to provide food compositions which allow the consumer to obtain a reduction in the blood cholesterol and triglyceride level, a preventive effect against cancer, in particular colon cancer, to reinforce immunity and intestinal flora of the consumer, to obtain antidiabetic effects (treatment and/or prevention of diabetes) and to ensure protection of the liver of the consumer.

A last aim of the invention is to propose a (physical) method for obtaining this milk ingredient which respects the organoleptic properties of the obtained milk ingredient and which is of simple and inexpensive conception and which has an improved yield in producing polar lipids, in particular phospholipids and sphingolipids which are particularly advantageous, which is expressed as a high weight percentage as compared with the dry matter percentage.

Characteristic Elements of the Invention

The present invention relates to a milk ingredient enriched in components of the milk fat globule membrane, i.e. enriched in polar lipids, in particular in phospholipids and in sphingolipids, but also depleted in proteins, in particular depleted in or without casein, while ensuring that the milk ingredient of the invention preserves the organoleptic properties of the dairy product from which it is derived.

By polar lipids, are meant lipids bearing a head or polar group at one of their ends. The most frequent polar lipids are phospholipids comprising phosphoric acid groups. Among these lipids, mention may be made of phosphoglycerides such as phosphatidylethanolamine, phosphatidylcholine, phosphatidylserine or phosphatidylinositol. The sphingolipids also include a polar head but no glycerol group.

Three subclasses of sphingolipids are distinguished: sphingomyelins, cerebrosides and gangliosides. Only sphingomyelins include a phosphoric acid group.

The sphingolipids mainly present in milk are sphingomyelin (SPH, or ceramide phosphorylcholine), ceramide glucosides, lactosyl ceramides and gangliosides.

The phospholipids mainly present are phosphatidylcholine (PC), phosphatidylethanolamine (PE), phosphatidylserine (PS) and phosphatidylinositol (PI). The other lipids present in the milk ingredient of the invention are neutral lipids (triglycerides) and cholesterol.

The proteins present in the product of the invention are milk proteins, i.e. mainly casein, lactalbumin and lactoglobulin.

The object of the invention relates to a milk ingredient enriched in these components from the membrane of the milk fat globules, in particular in polar lipids, i.e. a composition for which the concentration of these phospholipids, predominant components of polar lipids, is greater than 10% by weight, preferably greater than 20% by weight, preferably greater than 30% by weight, more particularly greater than 35%, 36%, 37%, 38% or 39% by weight, preferably about 39.4% by weight, calculated on the percentage of dry matter of the composition (total dry extract).

The other compounds present in the composition of the invention are water, proteins, carbohydrates, such as lactose, water-soluble vitamins, enzymes and ashes (minerals). In the subsequent text, lactose and ashes are also grouped together under the definition of non-protein defatted dry extract.

The milk ingredient of the invention is characterized by its high concentration of polar lipids, in particular phospholipids and of sphingolipids, as well as by its low relative concentration of its other milk components i.e., lactose, mineral salts but also proteins which are also preferably partly extracted during the polar lipid enrichment method.

Preferably, the product of the invention also comprises a low protein percentage, preferably less than 40%, more particularly less than 30%, preferably less than 28% (relatively to the dry matter content of the ingredient). Additionally, the composition also includes a certain percentage of saccharides (lactose), but which may also be extracted from the composition.

Advantageously, the proteins of the composition of the invention appear in a non-hydrolyzed form by the action of protease and/or peptidase enzymes, in order not to induce harmful effects on the organoleptic characteristics of the final obtained product (foodstuffs, pharmaceutical products, . . . ).

The milk ingredient of the invention may be present under solid form, preferably obtained by evaporation (thermal concentration and drying) of the water present in the composition of the invention, in order to obtain more stable products, more easy to handle and to dose, and less subject to biological denaturation.

Another aspect of the present invention relates to the method for obtaining the milk ingredient enriched in components from the milk fat globule membrane, and comprising particles (fat globules) of lipids having preferably a size less than 3 µm, comprised between about 1 µm and about 2.5 µm, in particular enriched in polar lipids, i.e. in phospholipids and in sphingolipids, preferably the milk ingredient of the invention. In particular, a milk ingredient enriched in polar lipids, i.e. a composition for which the concentration of phospholipids predominantly consisting of polar lipids, is greater than 10% by weight, preferably greater than 20% by weight, preferably greater than 30% by weight, or even greater than 35%, 36%, 37%, 38%, 39% by weight, preferably about 39.4% by weight, calculated on the dry matter percentage of the composition (total dry extract).

With the method of the invention, it is possible to obtain from a preferably pasteurized, milk cream, by combining different unitary operations, which are operations which do not alter the organoleptic properties of the obtained concentrated products and of the generated co-products, a milk ingredient enriched in these polar lipids, i.e. a composition for which the phospholipid concentration is greater than 10% by weight, preferably greater than 20% by weight, preferably greater than 30% by weight, greater than 35%, 36%, 37%, 38% or 39% by weight, preferably about 39.4% by weight, calculated on the dry matter percentage of the composition (total dry extract). This method comprises at least two successive and following steps of a treatment of a pasteurized milk cream:
- concentration by centrifugation,
- separation on a membrane (an ultrafiltration and/or ultrafiltration/diafiltration combination).

Preferably, the method of the invention comprises at least one concentration step by centrifugation and a step of ultrafiltration/diafiltration of the composition increasingly enriched in polar lipids.

According to an alternative embodiment of the method of the invention, the latter comprises one or more steps of concentration by centrifugation and several ultrafiltration/diafiltration steps.

According to a preferred embodiment of the invention, the method of the invention further includes one or more steps of washing of the concentrated extracts, by adding pure (non-buffered) water, preferably before a new step of concentration by centrifugation.

Advantageously, the method of the invention also includes one or more (successive) so-called deproteinization steps and capable to very strongly reduce the concentration of the initially present proteins.

Preferably, this deproteinization (coagulation) step includes a thermo-calcium treatment for precipitating casein and separating the latter from the medium; the thermo-calcium treatment comprises the addition of about 0.1% of calcium chloride (w/w), followed by heat treatment at about 70° C. for about 40 minutes, adjustment of the pH to about 5.2 by adding a food acid (citric acid or lactic acid or phosphoric acid or hydrochloric acid); the subsequent separation of the precipitated proteins is performed by centrifugal decantation (by means of a separator of the solid phase from the liquid phase).

In the thermo-calcium treatment step of the invention, addition of citric acid is preferred, but this step for coagulating the proteins may also be obtained by action of rennet and of the acids mentioned above.

Preferably, in the method of the invention, the pasteurized milk cream is also submitted to a preliminary heat treatment, for example by a heating to a temperature comprised between about 60° C. and about 75° C., preferably to a temperature comprised between about 65° C. and about 70° C., for an adequate period of time (about 5 to about 20 minutes, i.e. the duration of the continuous centrifugation). The inventors unexpectedly observed that a particularly high phospholipids concentration in the milk ingredient is obtained by the method of the invention, as a result of the passage of the phospholipids into the serum. This effect is particularly significant in the examples illustrated below and is not obtained when soft buttermilk powder is used as a raw material, as described in the state of the art. Further, the inventors also observed that the use of certain acidifiers was particularly effective in the coagulation step, but unlike the state of the art, coagulation by adding suitable rennet for obtaining coagulation (deproteinization step) is not effective for forming intermediate products.

A last aspect of the present invention relates to a pharmaceutical composition (functional food), a cosmetic composition, a food composition or a food additive comprising (in addition to the adequate pharmaceutical or food carriers) the milk ingredient enriched in polar lipids, in particular in phospholipids and sphingolipids, according to the invention, in particular a milk ingredient enriched in polar lipids, i.e. a composition having a phospholipid concentration greater than 10% by weight, preferably greater than 20% by weight, preferably greater than 30% by weight, greater than 35% by weight, 36%, 37%, 38%, 39% or even about 39.4% by weight calculated on the dry matter percentage of the composition (total dry extract). Said food composition or said additive for a food composition present equivalent or improved organoleptic or structural properties compared to those of standard food products, prepared without this ingredient.

The pharmaceutical composition will comprise an adequate pharmaceutical carrier and said ingredient (as an active ingredient) in an adequate proportion in order to induce a therapeutic or preventive effect on certain pathologies (in particular those described in the examples).

The present invention will be described in more detail in the exemplary embodiments below, presented as non-limiting illustrations of the invention, with reference to the enclosed figures.

DETAILED DESCRIPTION OF THE INVENTION

Example 1

Figure 1A:
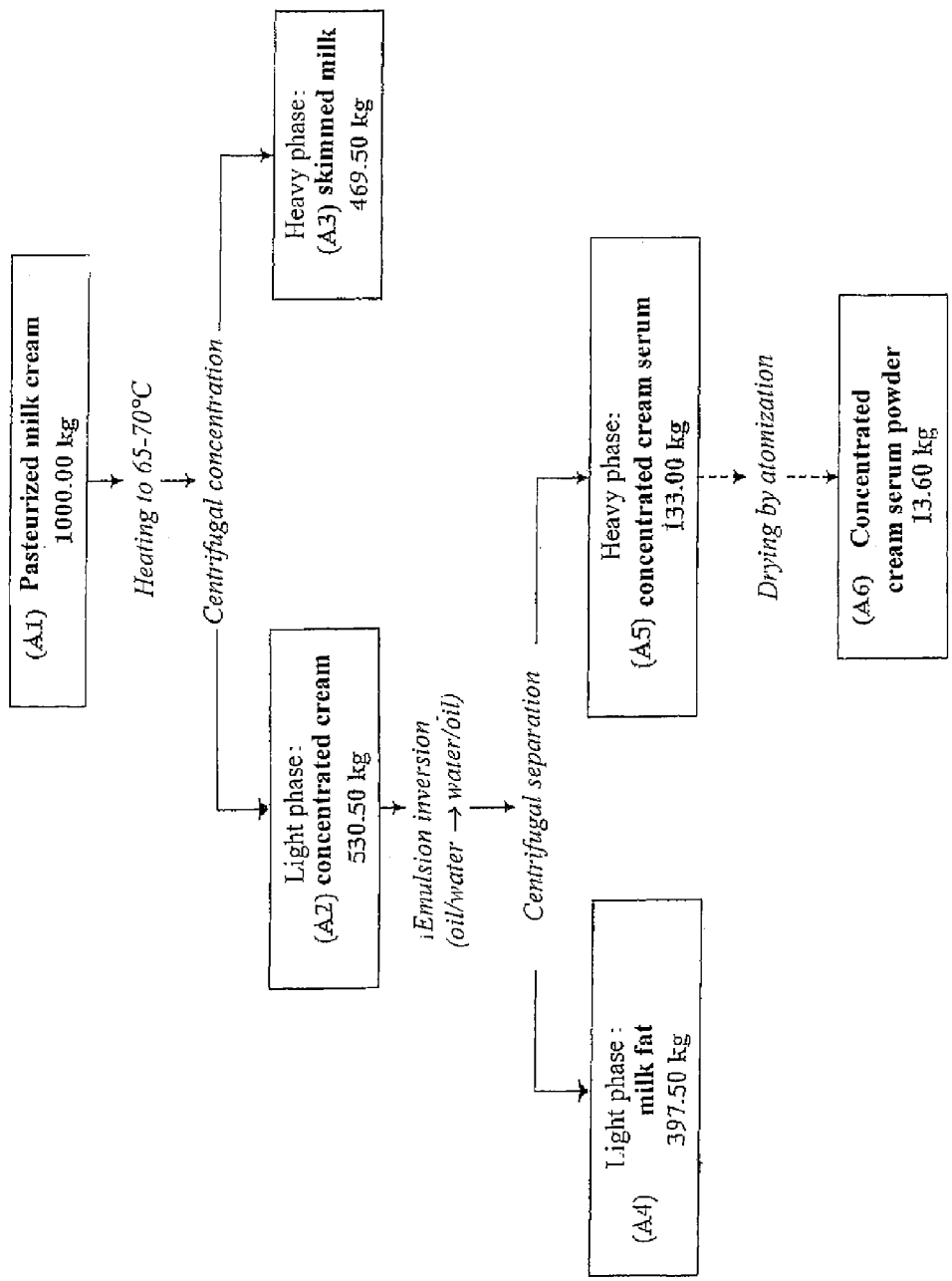
FIGS. 1a and 1b schematically represent the different steps of the method for preparing the milk ingredient of the invention from pasteurized milk cream. This ingredient is called a concentrated cream serum (FIG. 1a) and is advantageously concentrated by an ultrafiltration/diafiltration treatment (FIG. 1b).
Figure 1:
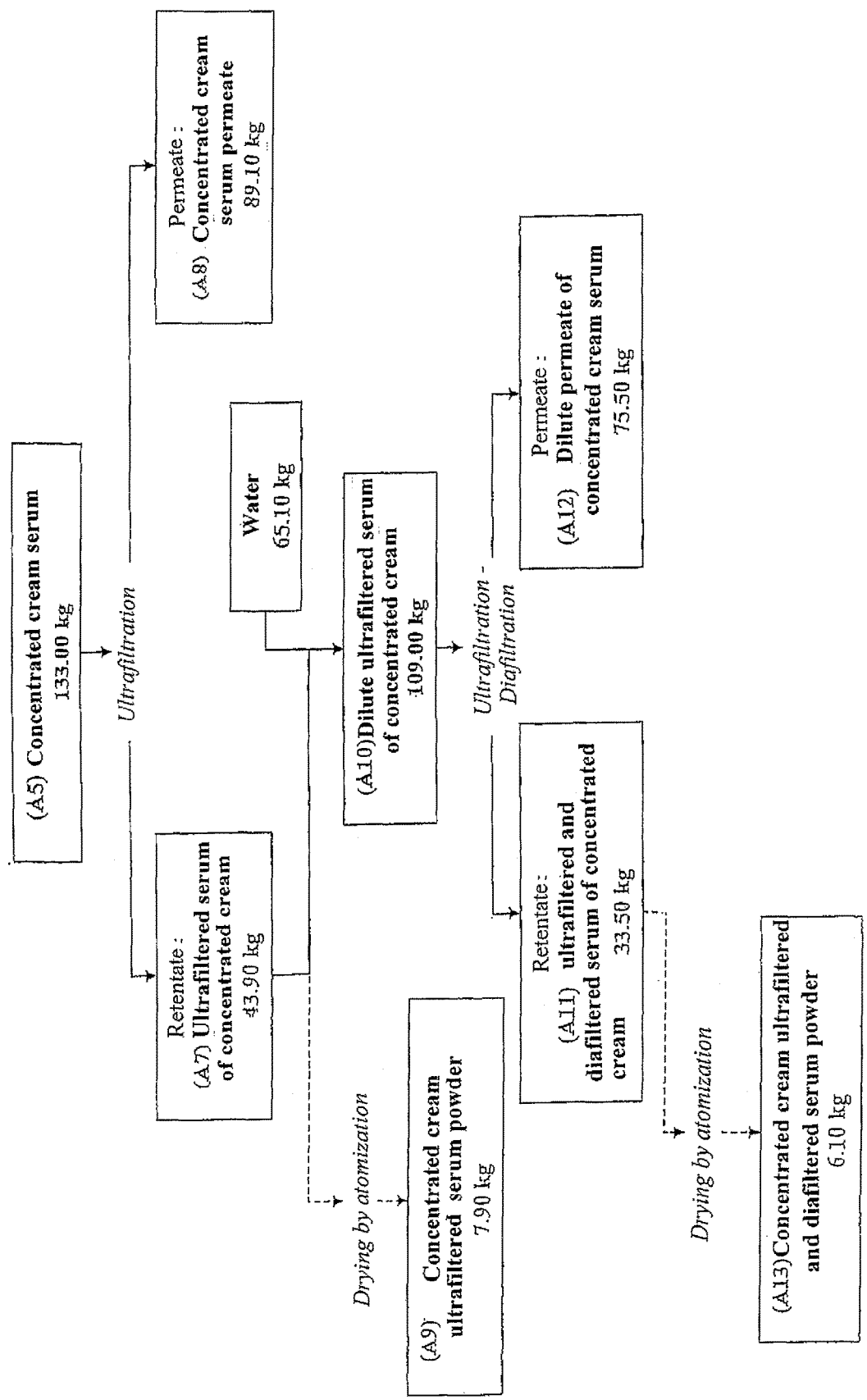

As illustrated in FIG. 1a, it is possible to advantageously obtain the milk ingredient of the invention from a preferably pasteurized, milk cream (A1).

About 1,000 kilograms of pasteurized milk cream (A1) are heated up to a temperature ideally comprised between about 65° C. and about 70° C. (for the whole step which is carried out continuously; this duration is of the order of 5-20 minutes.)

The thereby heated milk cream is submitted to a first centrifugation which allows a light concentrated cream phase (A2) and a heavy skimmed milk phase (A3) to be concentrated. The proportion of the light phase and of the heavy phase is essentially equivalent (about 530 kilograms of light phase (A2) and about 470 kilograms of heavy phase (A3)).

The light phase comprising concentrated cream (A2) as an <<oil-in-water>> emulsion is then transformed into a <<water-in-oil>> emulsion by a so-called emulsion inversion step; this step is followed by a second centrifugation allowing to re-concentrate the light phase (A2) into a new light phase (A4) and a new heavy phase (A5).

The so-called light phase (A4) essentially comprises milk fats; the heavy phase forming a concentrated cream serum (A5).

The proportion between this light phase (A4) and this heavy phase (A5) is about ¾-¼, (about 397 kilograms of light milk fat phase (A4) and about 133 kilograms of heavy phase (concentrated cream serum (A5)).

Next, the heavy phase (A5) is advantageously submitted to a drying step which provides a concentrated cream serum as a solid form (A6) (concentrated cream serum powder) for a weight of about fourteen kilograms (13.6 kilograms).

According to a first alternative embodiment of the invention (FIG. 1b), said heavy phase comprising concentrated cream serum (A5) is recovered and treated by an additional step comprising ultrafiltration allowing to recover a retentate and a permeate at the same time.

The retentate comprises an ultrafiltered serum of concentrated cream (A7) and the permeate comprises a permeate of concentrated cream serum (A8). The proportion between the retentate and the permeate is about ⅓-⅔ (about 44 kilograms of retentate and about 89 kilograms of permeate).

According to an alternative of the invention, it is also possible to carry out a direct drying of the ultrafiltered serum of concentrated cream (A7) to obtain a solid product: an ultrafiltered serum powder of concentrated cream (A9). The amount of powder obtained is about 8 kilograms (7.90 kilograms).

According to another preferred embodiment of the invention, the ultrafiltered serum of concentrated cream (A7) is diluted with water to form a diluted ultrafiltered serum of concentrated cream (A10) which is again concentrated by ultrafiltration (diafiltration).

This dilution is carried out by about 65 kilograms of water (i.e. 65.10 kg) added to about 44 kilograms (43.90 kg) of ultrafiltered serum of concentrated cream (A7) to form a solution of a diluted ultrafiltered serum of concentrated cream (A10) with a total weight of 109 kilograms.

The diluted ultrafiltered serum of concentrated cream (A10) is submitted to a second ultrafiltration (diafiltration) step, in order to obtain a new retentate (A11) and a new permeate (A12), the retentate comprising an ultrafiltered and diafiltered serum of concentrated cream (A11) and the permeate comprising a diluted permeate of concentrated cream serum (A12).

The proportion between the retentate (A11) and the permeate (A12) is about 30/70 (35.50 kilograms of retentate (A11) and 75.50 kilograms of permeate (A12)).

The retentate (A11) may be again submitted to a drying step in order to obtain a solid product: an ultrafiltered and diafiltered serum powder of concentrated cream (A13). The total weight of this powder is of about 6 kilograms (6.10 kilograms).

Table 1 shows the characteristics of the composition of different products obtained after the different steps carried out according to the method described above.

Table 1 shows, as a weight percentage, the contents of water, of total fat, of phospholipids (predominant part of the polar lipids included in the total fat), of defatted dry extract and of the constituents of this defatted dry extract, i.e. proteins, lactose and ashes.

It is observed that the concentrated cream serum (A5) submitted to the additional ultrafiltration and diafiltration steps is enriched in components from the milk fat globule membrane, i.e. enriched in polar lipids (phospholipids), as well as in total lipids (including the neutral lipids) and in proteins. This enrichment is essentially obtained to the detriment of contents of lactose above all and of ashes to a lesser extent.

The obtained products are milk ingredients rich in polar lipids. These milk ingredients respectively contain more than 7%, more than 11% and more than 14% of milk phospholipids, these percentages being expressed relatively to the dry matter.

Advantageously, the milk ingredient of the invention appears as a solid form and is obtained by a drying of a concentrated cream serum which is the result of a thermal concentration and a drying, preferably by atomization.

Figure 2:
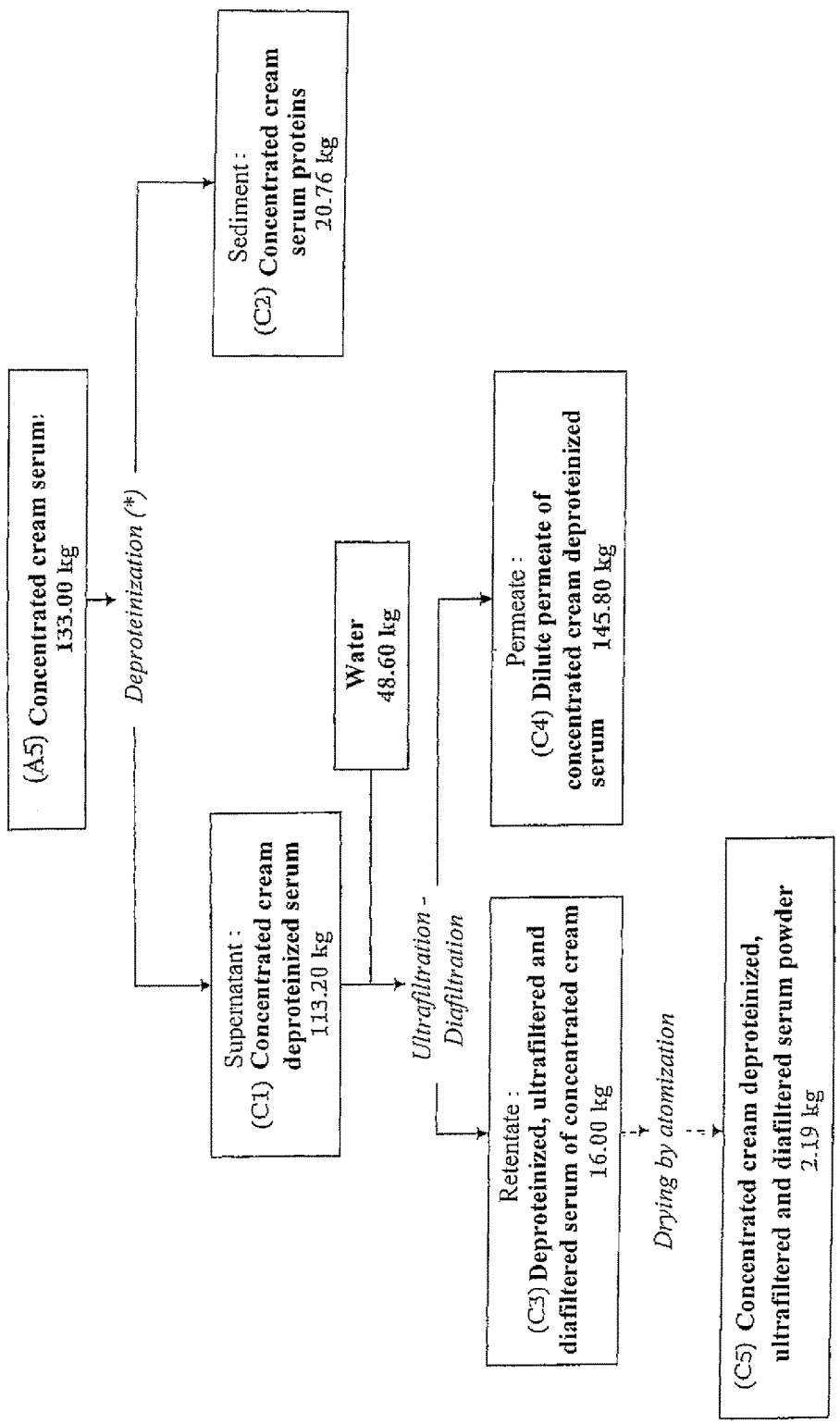
FIG. 2 schematically represents the steps of the method for obtaining the milk ingredient of the invention from a concentrated cream serum obtained by the treatments described in FIG. 1a. A deproteinization step and a concentration step by ultrafiltration and diafiltration allow to obtain a deproteinized, ultrafiltered and diafiltered serum of concentrated cream.

According to a second preferred embodiment of the invention illustrated in FIG. 2, 133 kg of concentrated cream serum (A5) are submitted to an extraction step of proteins (<<deproteinization>>) by a so-called <<thermo-calcium>> treatment comprising the addition of 0.1% (by weight) of calcium chloride, followed by a heating to a temperature of about 70° C., by adjusting the serum pH to about 5.2 by addition of citric acid, and by maintaining the serum at this temperature for a period of about 40 minutes.

Next, the precipitated proteins are extracted by an additional centrifugal decantation step (solid-liquid separator). A sediment of about 21 kg (20.76 kg) comprising the proteins of concentrated cream serum (C2) and a supernatant of about 113 kg (113.20 kg) of deproteinized serum of concentrated cream (C1) is thereby obtained.

The latter is then submitted to ultrafiltration/diafiltration, with dilution by means of about 49 kg (48.6 kg) of water. This operation provides 16 kg of retentate consisting of deproteinized, ultrafiltered and diafiltered serum of concentrated cream (C3) and about 146 kg (145.80 kg) of a diluted permeate of a deproteinized serum of concentrated cream (C4).

The retentate is submitted to an additional drying step (by atomization) to obtain about 2.2 kg (2.19 kg) of ultrafiltered and diafiltered deproteinized serum of concentrated cream (C5). The characteristics of the obtained products are presented in Table 2. The deproteinized, ultrafiltered and diafiltered serum of concentrated cream is a milk ingredient strongly enriched in milk polar lipids; its phospholipids content is greater than 35% by weight, this percentage being expressed relatively to the dry matter.

Figure 3:
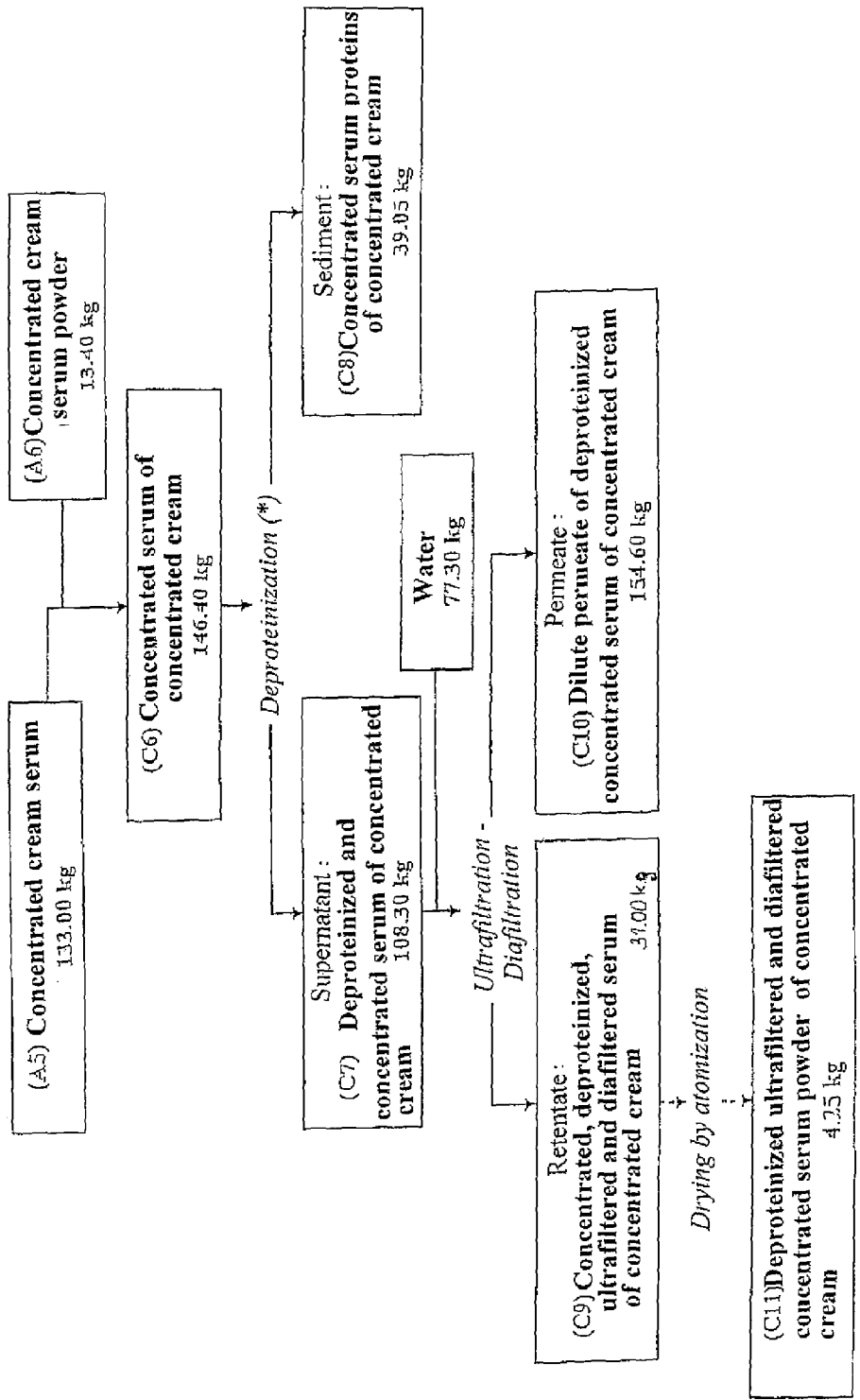
FIGS. 3a and 3b schematically represent the same method as the one described in FIG. 2 but carried out from a concentrated cream serum enriched in total dry extract; this method also provides a deproteinized, ultrafiltered and diafiltered concentrated serum of concentrated cream, identical to the one obtained by the treatments described in FIG. 2, without reducing the concentration factor of the polar lipids.
Figure 3:
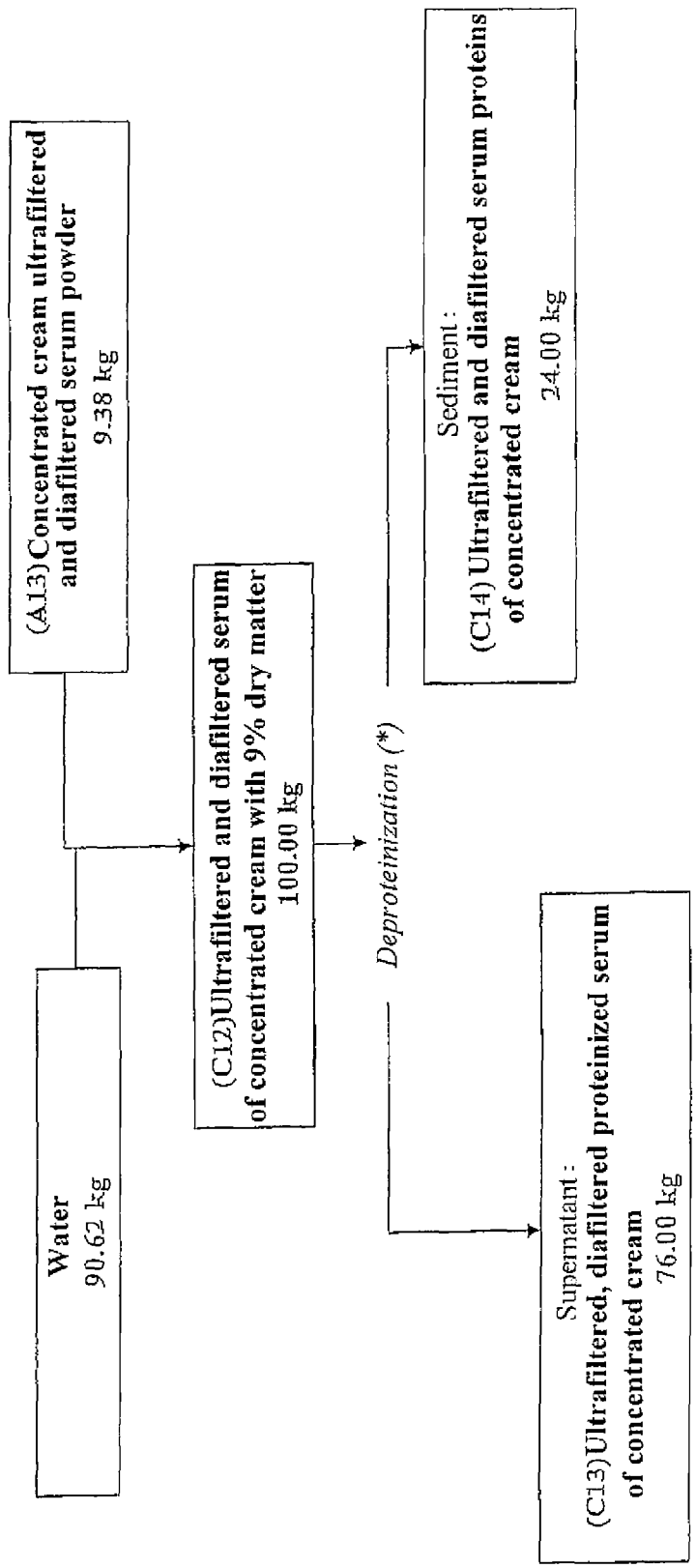

According to a third preferred embodiment of the invention represented in FIG. 3a, the concentrated cream serum (A5) (133 kg) may be combined with the concentrated serum powder (A6) (13.4 kg) to obtain about 146 kg (146.4 kg) of a concentrated cream serum (C6) with a higher dry matter content.

This product is submitted to a deproteinization step as described above to obtain a supernatant of about 108 kg (108.3 kg) comprising a concentrated and deproteinized serum of concentrated cream (C7) and of a sediment of about 39 kg (39.05 kg) comprising concentrated serum proteins of a concentrated cream (C8).

The supernatant is then submitted to an ultrafiltration/diafiltration step with addition of about 77 kg of water (77.3 kg) to obtain about 31 kg of a retentate comprising deproteinized, ultrafiltered and diafiltered concentrated serum of concentrated cream (C9) and about 154 kg (154.6 kg) of a diluted permeate of a deproteinized concentrated serum of concentrated cream (C10). The retentate may advantageously be submitted to an additional drying step by atomization to obtain a little more than 4 kilograms (4.25 kg) of a deproteinized, ultrafiltered and diafiltered concentrated serum powder of concentrated cream (C11). The characteristics of the obtained products are represented in Table 3. Again, the obtained deproteinized ultrafiltered and diafiltered concentrated serum of concentrated cream is a milk ingredient strongly enriched in milk polar lipids; its phospholipids content is greater than 35% by weight, this percentage being expressed relatively to the dry matter. The increase of the dry matter of the concentrated cream serum did not affect the concentration factor of the polar lipids recovered after deproteinization and ultrafiltration/diafiltration.

Alternatively, it is also possible to treat the ultrafiltered/diafiltered serum powder of concentrated cream (A13) (9.38 kg) by adding water (90.62 kg) to obtain 100 kg of an ultrafiltered/diafiltered serum of concentrated cream with 9% of dry matter (C12). This product is submitted to a deproteinization step (FIG. 3b) as described above to obtain 76 kg of a supernatant consisting of an ultrafiltered/diafiltered and deproteinized serum of concentrated cream (C13) and 24 kg of a sediment comprising ultrafiltered, diafiltered serum proteins of concentrated cream (C14). The characteristics of these latter products are represented in Table 4. The ultrafiltered, diafiltered and deproteinized serum of concentrated cream (C13) is the milk ingredient concentrated in polar lipids of this method; its milk phospholipids content is 0.95%, i.e. more than 20% by weight expressed on the dry matter.

Example 2

Figure 4:
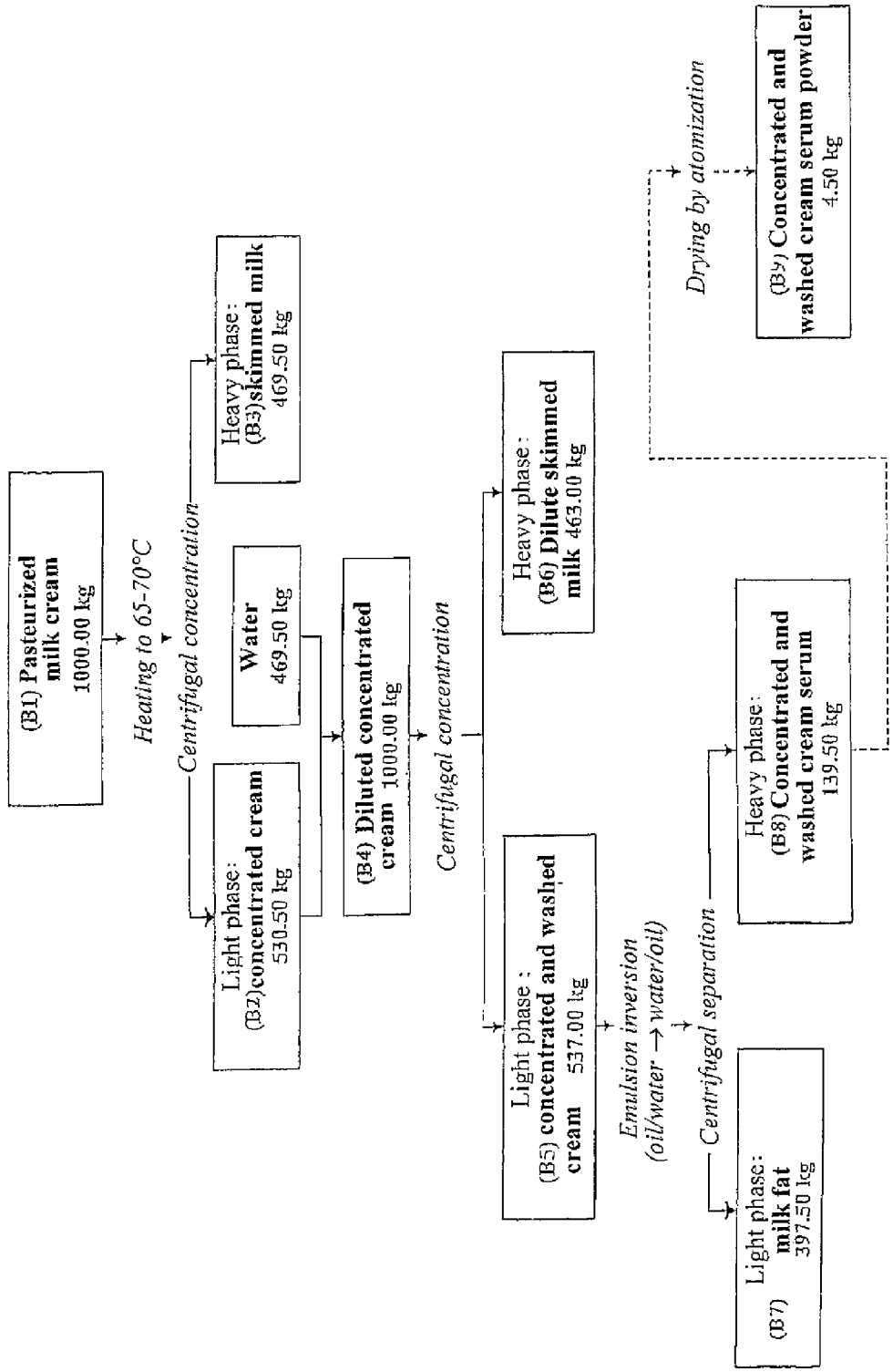
FIGS. 4a and 4b schematically represent the different steps of the method for obtaining the milk ingredient of the invention from a concentrated milk cream and diluted with water. This ingredient is called a concentrated and washed cream serum (FIG. 4a) and is advantageously concentrated by an ultrafiltration or optionally diafiltration treatment (FIG. 4b).
Figure 4:
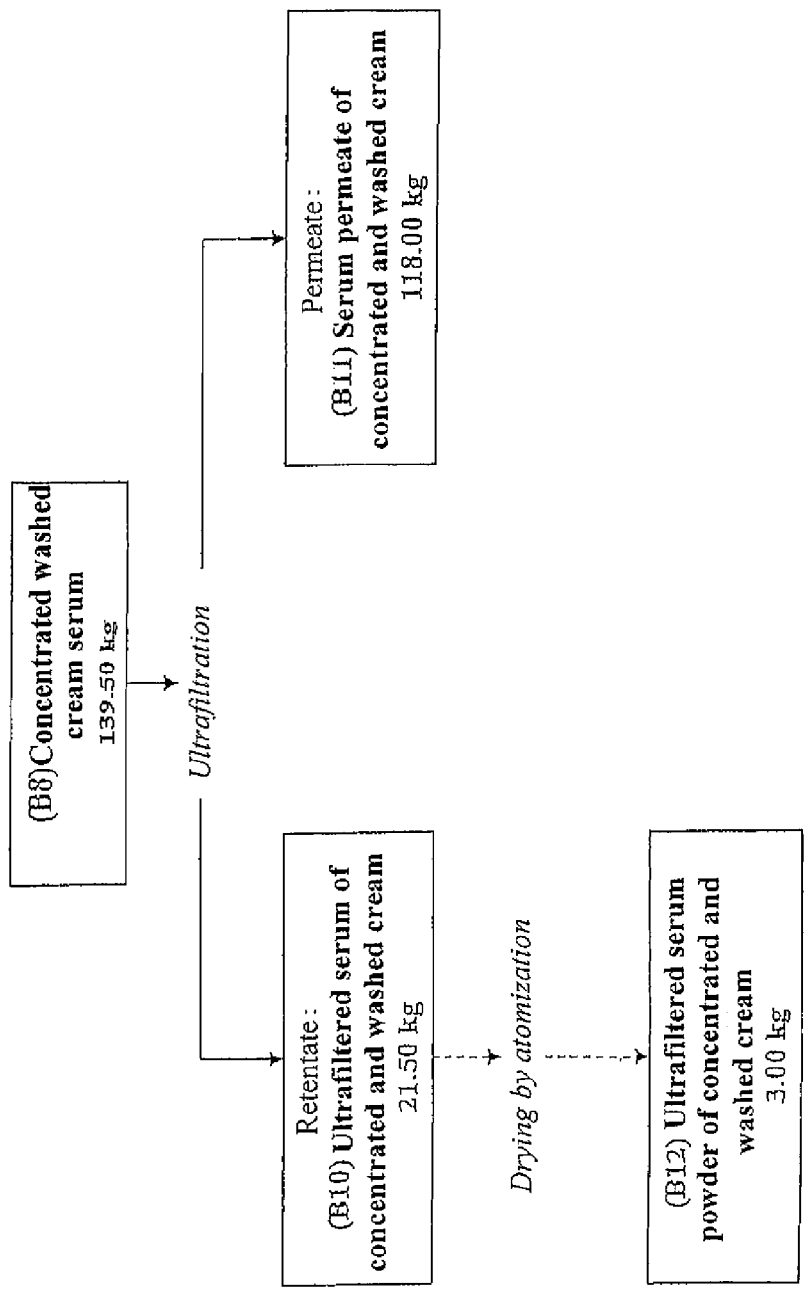

As illustrated in FIG. 4a, it is possible to also obtain the milk ingredient of the invention, according to an alternative embodiment of the one illustrated in Example 1. About 1,000 kg of pasteurized milk cream (B1) are submitted to a heat treatment similar to that of Example 1 and then to a first centrifugation, similar to that of Example 1, in order to obtain a light concentrated cream phase (B2) and a heavy skimmed milk phase (B3). The proportions are equivalent to those of Example 1. The light phase (B2) is diluted with a similar amount of pure (non-buffered) water in order to obtain a diluted concentrated cream (B4) (about 1,000 kg). This diluted concentrated cream (B4) is submitted to a second concentration by centrifugation so as to obtain a light phase comprising a concentrated and washed cream (B5) and of a heavy phase comprising a diluted skimmed milk (B6) (about 537 kg of concentrated and washed cream (B5) and about 463 kg of diluted skimmed milk (B6)).

The concentrated and washed cream (B6) is then submitted to an emulsion inversion step and to a new concentration by centrifugation, as described in Example 1. From the concentrated and washed cream (B5), a light phase consisting of milk fat (B7) (about 396 kg) and a heavy phase consisting of concentrated and washed cream serum (B8) (about 140 kg) are thereby obtained. This concentrated and washed cream serum may be submitted to a drying step, as described in Example 1 to obtain a concentrated and washed cream serum powder (B9) for a total weight of about 4.50 kg.

Said concentrated and washed cream serum (B8) may again be submitted to an ultrafiltration step, shown in FIG. 4b and as already described for Example 4, so as to obtain about 21.50 kg of retentate comprising a concentrated and washed cream ultrafiltered serum (B10) and about 118 kg of concentrated and washed cream serum permeate (B11). The retentate (concentrated and washed cream ultrafiltered serum (B10)) may also be submitted to a new drying step, as described in Example 1, to obtain a product as a solid form comprising a concentrated and washed cream ultrafiltered serum powder (B12) of a total weight of about 3.00 kg.

Table 5 shows the characteristics of the compositions of the products obtained according to the method of Example 2 illustrated in FIGS. 4a and 4b. The analyzed parameters are the same as those shown in Table 1. The concentrated and washed cream serum (B8) and the concentrated and washed cream ultrafiltered serum (B10) are milk ingredients strongly enriched in polar lipids from the milk fat globule membrane. The milk phospholipids content of the products is 0.62% and 3.90%, respectively, i.e. more than 19% and more than 27%, respectively, expressed on the basis of the dry material. The polar lipids concentration is obtained to the detriment of the defatted dry extract for the cream washing operation and to the detriment of the non-protein defatted dry extract for the ultrafiltration.

Advantageously, the following products, obtained during the method described above in Examples 1 and 2:
  concentrated cream serum,
  ultrafiltered and possibly diafiltered serum of concentrated cream,
  deproteinized, ultrafiltered and optionally diafiltered serum of concentrated cream,
  serum of concentrated and washed cream, and
  ultrafiltered serum of concentrated and washed cream, enriched in polar lipids from the milk fat globule membrane (phospholipids and sphingolipids), in their liquid form and/or optionally in their solid form, may be used in a food composition and incorporated with usual food components of a food composition intended for humans or animals.

It is thus possible to obtain food compositions (optionally lowered in certain fats harmful to health, in particular lowered in non-polar lipids), while maintaining the organoleptic properties of the standard products or providing improved organoleptic properties compared to the standard products.

The food ingredient of the invention, characterized by an emulsifying effect, may be used for improving the creaminess of food products, notably of dairy products, (either low-fat products or not), such as creams, yoghurts, drinkable yoghurts, cheeses, in particular cheese spreads or dairy desserts.

Additionally, the food ingredient provides for better retention of water in bakery/pastry products (milk rolls and brioches) thereby improving the preservation of the sponginess of these products compared to the standard products prepared without this food ingredient. Indeed, the inventors unexpectedly observe an improvement in the retention of water in the obtained products which enables the sponginess of these products to be better preserved while reducing their drying.

The milk ingredient of the invention may also be used for improving whippability of a full and low fat milk cream having been subject or not to a UHT sterilization heat treatment and to which the milk ingredient of the invention was incorporated.

A natural emulsifying effect of the milk is also observed, promoting emulsions of the <<oil-in-water>> type, obtained with the product as a dispersed powder in water or with the liquid serum product of the invention.

The inventors have shown that 5% fat creams, initially regenerated with milk fat, skimmed milk powder, water and either with concentrated cream serum powder (A6) on the one hand, or phospholipid-rich extracts (C5: deproteinized, ultrafiltered and diafiltered serum powder of concentrated cream or C11: deproteinized ultrafiltered and diafiltered concentrated serum powder of concentrated cream) on the other hand, did not have the same stability because of the natural size difference of their fat globules. For a content varying from 0.3 to 1.5% of concentrated cream serum powder (A6), the average size of the fat globules ranged from 5 to 3 μm, respectively. When the phospholipid source was represented by C5 extracts (deproteinized, ultrafiltered and diafiltered serum powder of concentrated cream) or C11 extracts (deproteinized, ultrafiltered and diafiltered concentrated serum powder of concentrated cream) in the same concentrations (0.3 to 1.5%), the average size of the fat globules ranged from about 2.5 to about 1 μm, respectively.

Furthermore, the milk ingredient of the invention has a high concentration in polar lipids, in particular in phospholipids and sphingolipids, with which the health condition of a patient may be improved significantly, or for sustaining the health condition of the patient directly consuming this ingredient or a food product containing this ingredient (H. Vesper et al. American Society for Nutritional Sciences, p. 1239-1250 (1999)).

With this ingredient enriched in sphingolipids (sphingomyelin, . . . ) it is possible to advantageously obtain a reduction in blood VLDL and LDL cholesterol and triglyceride levels, a preventive effect against cancer, in particular colon cancer, it is possible to reinforce immunity and intestinal flora, in particular cause a prebiotic effect, i.e. promote growth of beneficial intestinal flora (notably germs of the Bifidus type), as compared with pathogenic intestinal flora, and to prevent or treat digestive disorders (diarrhea).

Additionally, the ultraconcentration of phospholipids and sphingolipids in the milk ingredient may have antidiabetic effects (treatment and/or prevention of diabetes) and ensure protection of the liver.

A last aspect of the invention relates to a cosmetic composition or a pharmaceutical composition (nutraceutical or <<functional food>>) comprising an adequate pharmaceutical carrier and the milk ingredient of the invention, in particular intended for treating and/or preventing the aforementioned pathologies, as well as to a preventive or therapeutic treatment method of one of the aforementioned pathologies in mammals (including humans) wherein a sufficient amount of this composition is administered to a mammal (including a human) capable of suffering from these pathologies.

TABLE 1

| | Weight % | | | | | | |
|---|---|---|---|---|---|---|---|
| | Water | Total fat | Including phospholipids | Defatted dry extracts | Including proteins | Including lactose | Including ashes |
| (A1) Pasteurized milk cream | 54.90% | 40.00% | 0.22% | 5.10% | 1.83% | 2.84% | 0.42% |
| (A2) Concentrated milk cream | 22.88% | 75.00% | 0.35% | 2.13% | 0.76% | 1.18% | 0.18% |
| (A3) Skimmed milk | 91.13% | 0.40% | 0.07% | 8.47% | 3.04% | 4.72% | 0.71% |
| (A4) Milk fat | 0.37% | 99.60% | 0.23% | 0.03% | 0.01% | 0.02% | 0.00% |
| (A5) Concentrated cream serum | 90.17% | 1.45% | 0.75% | 8.38% | 3.01% | 4.67% | 0.70% |
| (A6) Concentrated cream serum powder | 4.00% | 14.17% | 7.33% | 81.83% | 29.40% | 45.62% | 6.82% |
| (A7) Concentrated cream ultrafiltered serum | 82.69% | 4.24% | 2.10% | 13.07% | 8.30% | 3.60% | 1.17% |
| (A9) Concentrated cream ultrafiltered serum powder | 4.00% | 23.51% | 11.65% | 72.49% | 46.03% | 19.97% | 6.49% |
| (A11) Concentrated cream ultrafiltered and diafiltered serum | 82.46% | 5.00% | 2.75% | 12.54% | 10.70% | 0.70% | 1.14% |
| (A13) Concentrated cream ultrafiltered and diafiltered serum powder | 4.00% | 27.40% | 15.00% | 68.60% | 58.53% | 3.83% | 6.24% |

TABLE 2

| | Weight % | | | | | | |
|---|---|---|---|---|---|---|---|
| | Water | Total fat | Including phospholipids | Defatted dry extracts | Including proteins | Including lactose | Including ashes |
| (A5) Concentrated cream serum | 90.17% | 1.45% | 0.75% | 8.38% | 3.01% | 4.67% | 0.70% |
| (C1) Deproteinized serum of concentrated cream | 92.08% | 1.43% | 0.78% | 6.49% | 0.90% | 4.73% | 0.86% |

TABLE 2-continued

| | Weight % | | | | | | |
|---|---|---|---|---|---|---|---|
| | Water | Total fat | Including phospholipids | Defatted dry extracts | Including proteins | Including lactose | Including ashes |
| (C2) Concentrated cream serum proteins | 79.62% | 1.45% | 0.72% | 18.93% | 14.00% | 4.10% | 0.83% |
| (C3) Concentrated cream deproteinized, ultrafiltered and diafiltered serum | 86.80% | 8.70% | 5.20% | 4.50% | 3.60% | 0.65% | 0.25% |
| (C4) Concentrated cream deproteinized serum diluted permeate | 95.47% | <0.10% | <0.10% | 4.50% | 0.25% | 3.60% | 0.65% |
| (C5) Concentrated cream deproteinized, ultrafiltered and diafiltered serum powder | 3.50% | 63.60% | 38.00% | 32.90% | 26.30% | 4.76% | 1.84% |

TABLE 3

| | Weight % | | | | | | |
|---|---|---|---|---|---|---|---|
| | Water | Total fat | Including phospholipids | Defatted dry extracts | Including proteins | Including lactose | Including ashes |
| (C6) Concentrated serum of concentrated cream | 82.30% | 2.60% | 1.35% | 15.10% | 5.30% | 8.51% | 1.29% |
| (C7) Concentrated and deproteinized serum of concentrated cream | 85.90% | 2.60% | 1.45% | 11.50% | 1.35% | 8.75% | 1.40% |
| (C8) Concentrated serum proteins of concentrated cream | 72.20% | 2.50% | 1.00% | 25.30% | 16.00% | 7.90% | 1.40% |
| (C9) Deproteinized, ultrafiltered and diafiltered concentrated serum of concentrated cream | 86.75% | 8.80% | 5.30% | 4.45% | 3.60% | 0.60% | 0.25% |
| (C10) Dilute permeate of deproteinized concentrated serum of concentrated cream | 92.83 | <0.10% | <0.10% | 7.15% | 0.25% | 6.00% | 0.90% |
| (C11) Deproteinized, ultrafiltered and diafiltered concentrated serum powder of concentrated cream | 3.00% | 64.42% | 38.80% | 32.58% | 26.35% | 4.39% | 1.83% |

TABLE 4

| | Weight % | | | | | | |
|---|---|---|---|---|---|---|---|
| | Water | Total fat | Including phospholipids | Defatted dry extracts | Including proteins | Including lactose | Including ashes |
| (A13) Ultrafiltered and diafiltered serum powder of concentrated cream | 4.00% | 27.40% | 15.00% | 68.60% | 58.53% | 3.83% | 6.24% |
| (C12) Ultrafiltered and diafiltered serum of concentrated cream | 91.00% | 2.57% | 1.40% | 6.43% | 5.48% | 0.36% | 0.59% |
| (C13) Ultrafiltered, diafiltered and deproteinized serum of concentrated cream with 9% dry matter | 95.58% | 1.85% | 0.95% | 2.57% | 1.59% | 0.38% | 0.60% |
| (C14) Ultrafiltered and diafiltered serum proteins of concentrated cream | 76.75% | 4.30% | 2.70% | 18.95% | 18.00% | 0.35% | 0.60% |

TABLE 5

| | Water | Total fat | Including phospholipids | Defatted dry extracts | Including proteins | Including lactose | Including ashes |
|---|---|---|---|---|---|---|---|
| (B1) Pasteurized milk cream | 54.90% | 40.00% | 0.22% | 5.10% | 1.83% | 2.84% | 0.42% |
| (B2) Concentrated milk cream | 22.88% | 75.00% | 0.35% | 2.13% | 0.76% | 1.18% | 0.18% |
| (B3) Skimmed milk | 91.13% | 0.40% | 0.07% | 8.47% | 3.04% | 4.72% | 0.71% |
| (B4) Dilute concentrated cream | 59.09% | 39.79% | 0.19% | 1.13% | 0.40% | 0.63% | 0.09% |
| (B5) Concentrated and washed cream | 25.52% | 74.00% | 0.32% | 0.48% | 0.17% | 0.27% | 0.04% |
| (B6) Dilute skimmed milk | 98.05% | 0.15% | 0.03% | 1.80% | 0.65% | 1.00% | 0.15% |
| (B7) Milk fat | 0.39% | 99.60% | 0.22% | 0.01% | 0.00% | 0.01% | 0.00% |
| (B8) Concentrated and washed cream serum | 96.90% | 1.30% | 0.62% | 1.80% | 0.65% | 1.00% | 0.15% |
| (B9) Concentrated and washed cream serum powder | 4.00% | 40.26% | 19.20% | 55.74% | 20.02% | 31.07% | 4.64% |
| (B10) Concentrated and washed cream ultrafiltered serum | 86.50% | 8.00% | 3.90% | 5.50% | 4.30% | 0.60% | 0.60% |
| (B12) Concentrated and washed cream ultrafiltered serum powder | 4.00% | 56.89% | 27.73% | 39.11% | 30.58% | 4.27% | 4.27% |

Translation of the Figures

| | |
|---|---|
| Crème de lait pasteurisée | Pasteurized milk cream |
| Chauffage à 65-70° C. | Heating to 65-70° C. |
| Concentration centrifuge | Centrifugal concentration |
| Phase légère: crème concentrée | Light phase: concentrated cream |
| Phase lourde: lait écrémé | Heavy phase: skimmed milk |
| Inversion de l'émulsion (huile/eau →eau/huile) | Emulsion inversion (oil/water → water/oil) |
| Séparation centrifuge | Centrifugal separation |
| Phase légère: (A4) matière grasse de lait | Light phase: (A4) milk fat |
| Phase lourde: | Heavy phase: |
| (A5) sérum de crème concentré | (A5) concentrated cream serum |
| Séchage par atomisation | Drying by atomization |
| Poudre de sérum de crème concentrée | Concentrated cream serum powder |
| (A5) Sérum de crème concentrée | (A5) Concentrated cream serum |
| Ultrafiltration | Ultrafiltration |
| Rétentat: (A7) Sérum ultrafiltré de crème concentrée | Retentate: (A7) Ultrafiltered serum of concentrated cream |
| Perméat: (A8) Perméat de serum de crème concentre | Permeate: (A8) Concentrated cream serum permeate |
| Eau | Water |
| (A10) Sérum ultrafiltré dilué de crème concentre | (A10) Dilute ultrafiltered serum of concentrated cream |
| Diafiltration | Diafiltration |
| Rétentat: (A11) Sérum ultrafiltré et diafiltré de crème concentré | Retentate; (A11) ultrafiltered and diafiltered serum of concentrated cream |
| (A13) Poudre de sérum ultrafiltré et diafiltré de crème concentrée | (A13) Concentrated cream ultrafiltered and diafiltered serum powder |
| Déprotéinisation (*) | Deproteinization (*) |
| Culot: (C2) Protéines de sérum de crème concentre | Sediment: (C2) Concentrated cream serum proteins |
| Surnageant: (C1) Sérum déprotéiné de crème concentre | Supernatant: (C1) Concentrated cream deproteinized serum |
| Rétentat: (C3) sérum déprotéiné, ultrafiltré, et diafiltré de crème concentrée | Retentate: (C3) Deproteinized, ultrafiltered and diafiltered serum of concentrated cream |
| Perméat: (C4) Perméat dilué de sérum déprotéiné de crème concentré | Permeate: (C4) Dilute permeate of concentrated cream deproteinized serum |
| (C5) Poudre de sérum déprotéiné, ultrafiltré et diafiltré de crème concentrée | (C5) Concentrated cream deproteinized, ultrafiltered and diafiltered serum powder |
| (C6) Sérum concentre de crème concentrée | (C6) Concentrated serum of concentrated cream |
| Surnageant: (C7) Sérum concentré et déprotéiné de crème concentrée | Supernatant: (C7) Deproteinized and concentrated serum of concentrated cream |
| Culot: (C8) Protéines de sérum concentré de crème concentrée | Sediment: (C8) Concentrated serum proteins of concentrated cream |
| Rétentat: (C9) Sérum concentré, déprotéiné, ultrafiltré, et diafiltré de crème concentrée | Retentate: (C9) Concentrated, deproteinized, ultrafiltered and diafiltered serum of concentrated cream |
| Perméat: (C10) Perméat dilué de sérum concentré, déprotéiné | Permeate: (C10) Dilute permeate of deproteinized concentrated serum of concentrated cream |
| (C11) Poudre de sérum concentré, déprotéiné, ultrafiltré et diafiltré de crème concentrée | (C11) Deproteinized ultrafiltered and diafiltered concentrated serum powder of concentrated cream |
| (C12) Sérum ultrafiltré et diafiltré de crème concentrée à 9% de matière sèche | (C12) Ultrafiltered and diafiltered serum of concentrated cream with 9% dry matter |
| Culot: (C14) Protéines de sérum ultrafiltré et diafiltré de crème concentrée | Sediment: (C14) Ultrafiltered and diafiltered serum proteins of concentrated cream |
| Surnageant: (C13) Sérum ultrafiltré, diafiltré et déprotéiné de crème concentrée | Supernatant: (C13) Ultrafiltered, diafiltered proteinized serum of concentrated cream |
| (B4) Crème concentrée diluée | (B4) Diluted concentrated cream |
| Phase légère: (B5) Crème concentrée et lavée | Light phase: (B5) concentrated and washed cream |
| Phase lourde: (B6) Lait écrémé dilué | Heavy phase: (B6) Dilute skimmed milk |
| Phase lourde: (B8) Sérum de crème concentrée et lavée | Heavy phase: (B8) Concentrated and washed cream serum |
| (B9) Poudre de sérum de crème concentrée et lavée | (B9) Concentrated and washed cream serum powder |
| (B8) Sérum de crème concentrée et lavée | (B8) Concentrated washed cream serum |

| | |
|---|---|
| Rétentat: (B10) Sérum ultrafiltré de crème concentrée et lavée | Retentate: (B10) Ultrafiltered serum of concentrated and washed cream |
| Perméat: (B11) Perméat de sérum de crème concentrée et lavée | Permeate: (B11) Serum permeate of concentrated and washed cream |
| (B12) Poudre de sérum ultrafiltré de crème concentrée et lavée | (B12) Ultrafiltered serum powder of concentrated and washed cream |

The invention claimed is:

1. A method to obtain a dairy ingredient enriched with polar lipids, wherein the weight percentage of phospholipids is higher than 36% based on the percentage of dry matter of the ingredient, and wherein a pasteurized milk cream is subjected to a physical treatment that comprises the following steps:

centrifugating a pasteurized milk cream that results into a light phase of a concentrated cream, a heavy phase of a skimmed milk;

obtaining an emulsion inversion of the light phase of a concentrated cream into a water in oil emulsion;

centrifugally separating the light phase of the concentrated cream to obtain a light phase of milk fat and a heavy phase of concentrated cream serum;

followed by the steps of:

extracting proteins from the heavy phase of concentrated cream serum through a thermocalcic treatment comprising an addition of calcium chloride, followed by a heat treatment at about 70° C. during 40 minutes, and a PH adjustment to about 5.2 through acid adjunction selected from the group consisting of an adjunction of citric acid, phosphoric acid, or a mixture thereof;

extracting the precipitated proteins by centrifugal decantation to obtain a sediment of proteins of concentrated cream serum and a supernatant of deproteinized serum of concentrated cream; and ultrafiltering and diafiltering with water dilution of the supernatant of deproteinized serum of concentrated cream to obtain a diluted permeate of a deproteinized serum of concentrated cream and a retentate of deproteinized ultrafiltered and diafiltered serum of concentrated cream;

or followed by the steps of:

drying by atomizing the heavy phase of concentrated cream serum obtained after the second centrifugation step into a concentrated cream serum powder;

combining the heavy phase of concentrated cream serum obtained after the second centrifugation step and the concentrated cream serum powder to obtain a concentrated cream serum;

extracting proteins from the concentrated cream serum through a thermocalcic treatment comprising an addition of calcium chloride, followed by a heat treatment at about 70° C. during 40 minutes, and a PH adjustment to about 5.2 through acid adjunction selected from the group consisting of an adjunction of citric acid, phosphoric acid, or a mixture thereof;

extracting the precipitated proteins by centrifugal decantation to obtain a sediment of concentrated serum proteins of a concentrated cream and a supernatant of a concentrated and deproteinized serum of concentrated cream; and ultrafiltering and diafiltering with water dilution of the supernatant of concentrated and deproteinized serum of concentrated cream to obtain a diluted permeate of a deproteinized concentrated serum of concentrated cream and a retentate of deproteinized ultrafiltered and diafiltered concentrated serum of concentrated cream.

2. The method according to claim 1, further comprising a drying step atomizing the retentate of deproteinized ultrafiltered and diafiltered serum of concentrated cream into a deproteinized ultrafiltered and diafiltered cream serum powder of concentrated cream.

3. The method according to claim 1, wherein the polar lipids comprise a mixture of phospholipids and sphingolipids.

4. The method of claim 1, which further comprises a drying step atomizing the retentate of deproteinized ultrafiltered and diafiltered concentrated cream into a deproteinized ultrafiltered and diafiltered concentrated serum powder of concentrated cream.

5. The method of claim 1, wherein prior to centrifugation, the pasteurized milk cream is submitted to a heating step at a temperature between 65° C. and 70° C.

6. The method according to claim 1, wherein the weight percentage of phospholipids is 38%.

7. The method according to claim 4, wherein the weight percentage of phospholipids is 38.8%.

* * * * *